United States Patent [19]

Powell

[11] Patent Number: 4,822,605

[45] Date of Patent: Apr. 18, 1989

[54] COMPOSITIONS AND METHODS EMPLOYING THE SAME FOR THE TREATMENT OF VIRAL AND CANCEROUS SKIN LESIONS AND THE LIKE

[75] Inventor: Maxwell M. Powell, Great Neck, N.Y.

[73] Assignee: Exovir, Inc., Great Neck, N.Y.

[21] Appl. No.: 830,662

[22] Filed: Feb. 18, 1986

[51] Int. Cl.$^4$ ................ A61K 45/05; A61K 45/02
[52] U.S. Cl. ......................... 424/85.2; 424/85.1; 424/85.4; 424/85.5; 424/85.7
[58] Field of Search ............... 424/85, 85.1, 85.2, 424/85.5, 85.6, 85.7

[56] References Cited

U.S. PATENT DOCUMENTS

| | | | |
|---|---|---|---|
| 4,457,916 | 7/1984 | Hayashi et al. | 424/101 |
| 4,480,032 | 10/1984 | Yabrov | 424/85 |
| 4,481,137 | 11/1984 | Ohnishi et al. | 435/68 |
| 4,495,282 | 1/1985 | Ohnishi et al. | 435/68 |
| 4,507,281 | 3/1985 | Asculai et al. | 435/68 |
| 4,529,594 | 7/1985 | Hayashi et al. | 424/85 |
| 4,650,674 | 3/1987 | Aggarwal et al. | 424/85 |

FOREIGN PATENT DOCUMENTS 0128009 12/1984 European Pat. Off. .
0149551 7/1985 European Pat. Off. .

*Primary Examiner*—Blondel Hazel
*Attorney, Agent, or Firm*—Cooper & Dunham

[57] ABSTRACT

A composition containing an antiviral and an antitumor agent is useful when topically applied for the treatment of tumors and cancers, particularly for the treatment of viral or cancerous skin disorders and skin manifestations thereof. Interferon is usefully employed in these compositions in combination with the antitumor agent. Antitumor agents which are useful include interleukin, such as Interleukin II, tumor necrosis factor (TNF), target cell lysis factor (TCLF) and carcino-breaking factor (CBF). These compositions are especially usefully applied by topical application to the skin manifestation of the viral or cancerous skin disorder.

22 Claims, No Drawings

COMPOSITIONS AND METHODS EMPLOYING THE SAME FOR THE TREATMENT OF VIRAL AND CANCEROUS SKIN LESIONS AND THE LIKE

BACKGROUND OF THE INVENTION

This invention relates to compositions and methods for treating viral or cancerous skin disorders. In particular, this invention relates to pharmaceutical compositions useful for treating viral and/or cancerous skin disorders by topical administration of said compositions to the affected area.

Virus-induced skin disorders are widely known. Dermotropic viruses include poxvirus, measles virus, varicella-zoster, coxsackievirus, echovirus, herpes simplex, rubella adenovirus, papillomavirus and molluscum contagiosum. A variety of skin disordes, such as psoriasis, eczema, conjunctivitis, keratoconjunctivitis, gingivostoma, herpes labialis, herpes keratitis, genital herpes, chicken pox, shingles, milker's nodules, cowpox are therapeutically treated with compositions of this invention which comprise anti-viral agents for topical application. Further, various cancerous skin disorders such as melanoma, basal cell carcinoma, squamous cell carcinoma, Kaposi sarcoma and the like are also amenable to treatment by the topical application of compositions of this invention.

Surface active agents (surfactants) have recently been discovered as effective in reducing the infectivity of certain viruses. Particularly effective are the nonionic surfactants, those with ether or amide linkages between the hydrophilic and hydrophobic portions of the molecule. The therapeutic effect of these surfactants probably resides in their ability to interact with and dissolve the lipid-containing envelope of the virus, and in their ability to partially destroy the nucleocapsid of the virus.

When so employed, surfactants have been applied to the skin surface to contact the uppermost layer of infected cells. Because of a dilution effect, cells below the surface do not readily receive sufficient amounts of the surfactant to destroy the virus particles. Therefore, it would be beneficial to provide an adjuvant which aids in moving the surfactant or other medicament therewith to infected cells below the skin surface. A suitable such adjuvant is dimethyl sulfoxide.

Perhaps the best known of the antiviral agents are the interferons. Human interferons are known to protect cells against viral infections. Human interferons are produced by cells in reaction to the presence of specific inducers, such as viruses. They may be produced in vivo by the cells of living organisms, or they may be produced in vitro by cell cultures in response to the presence of the inducer. There are now known to be three major varieties of human interferon: leukocyte or alpha, fibroblast or beta, and immune or gamma interferon. There are also known to be several sub-varieties of human leukocyte and fibroblast interferon.

Human interferon is relatively nontoxic and nonantigenic in humans. It is also extremely effective against a broad spectrum of viruses, including herpes simplex virus, even at very low concentrations.

Various uses of interferon for its antiviral effect are known, see for example, U.S. Pat. No. 4,053,582 (Stickl) which discloses a method for treating herpes simplex infections in humans by administering attenuated fowl pox virus to the patient. The attenuated virus induces the patient to produce his own interferon. The herpetic lesions heal within a short time after induction.

U.S. Pat. Nos. 4,061,538 (Dorner et al.) and 4,184,917 (Dorner et al.) disclose a method of treating herpes simplex viral infections by administering structurally modified interferons to the patient. In these patients, the modified interferons are administered systematically to the patient.

Further, topical administration of human interferon in compositions containing antiviral surfactants has been shown to be effective in the treatment of skin disorders due to herpes simplex viral infection, see U.S. Pat. No. 4,507,281.

Tumor Necrosis Factor (TNF), an antitumor agent, was recently discovered by Carswell et al, Proc. Natl. Acad. Sci. U.S.A. Vol. 72, No. 9 pp. 3666–3670 (1975). TNF was found in the serum of mice, rats and rabbits which had been sensitized with an immunopotentiator and then treated with an endotoxin. Purified TNF, while having no toxic effect on the treated individual, exerts a potent activity against tumors transplanted into those individuals; the activity is not species specific. The advantage in having no cytotoxic effect against normal cells while having significant antitumor activity makes TNF an important candidate for the treatment of the skin manifestations of various types of cancers. Uses of TNF and related antitumor or anticancer agents are disclosed in U.S. Pat. Nos. 4,309,418; 4,447,355; 4,457,916; 4,481,137; 4,495,282 and 4,529,594. U.S. Pat. No. 4,481,137 discloses that several factors considered as promising therapeutic agents for tumors, e.g. lymphotoxin, TNF, interferon, had been obtained from reticulo-endothelial cells and that carcono-breaking factor (CBF) as a mixture containing lymphotoxin and TNF has been obtained from a culture of lymphoblasts grown in immune suppressed hamsters. Another antitumor agent called target cell lysis factor (TCLF) is disclosed in U.S. Pat. No. 4,495,282 as being comprised of lymphotoxin and human TNF.

Other anti-tumor agents useful in the practices of this invention, in addition to interferon and TNF, include the interleukins, particularly Interleukin II, see U.S. Pat. No. 4,518,584. Interleukin II which has been demonstrated to be an antitumor agent, is especially useful in the practices of this invention.

It is an object of the present invention to provide a pharmaceutical composition useful for the treatment of cancerous skin disorders such as by topical administration of said composition to the skin manifestations of such disorders.

It is another aspect of the present invention to provide a method for treating, viral and/or cancerous skin disorders by topically applied therapeutic compositions.

SUMMARY OF THE INVENTION

A composition comprising an antitumor agent and an antiviral surfactant is useful for the treatment of tumors and cancers, particularly for the treatment of viral or cancerous skin disorders and skin manifestations thereof.

A suitable such composition for the treatment of viral or cancerous skin disorders would comprise an effective antitumor amount of the antitumor agent, e.g. about $10^2$ IU to $10^8$ IU of Tumor Necrosis Factor, and about 0.1% to 20% by weight of an antiviral surfactant, together with a physiologically acceptable carrier. Desirably, these would be included in such compositions about $10^2$ to about $10^8$ IU of human interferon.

A method for treating viral or cancerous skin disorders employing the compositions of this invention would include topically administering to the skin or the affected area an effective amount of the composition.

DETAILED DESCRIPTION OF THE INVENTION

The compositions of one embodiment of this subject invention contains effective amounts of Tumor Necrosis Factor (TNF), human interferon, an antiviral surface active agent, and a physiologically acceptable carrier. The TNF may be natural or synthetic TNF, i.e. TNF produced by recombinant DNA technology. The compositions may also contain any, natural or synthetic, of the known varieties or sub-varieties of human interferon. Thus, the compositions may contain natural and/or synthetic TNF and natural and/or synthetic alpha- or human leukocyte interferon, and/or beta- or fibroblast interferon, and/or gamma- or immune interferon. An effective dose of TNF for treatment in accordance with the practices of the subject invention would be about $10^2$ to $10^8$ IU, more or less. An effective dosage of human interferon when present in the compositions in accordance with the practices of the subject invention would be about $10^2$ to $10^8$, preferably about $10^4$ to $10^8$, I.U.

Although TNF is the preferred antitumor agent in the practices of this invention, particularly in combination with human interferon, e.g. alpha- and/or beta- and/or gamma-interferon, other antitumor agents in combination with the antiviral surfactant, alone or in combination with interferon or with another antitumor agent are also useful. As indicated hereinabove, other antitumor agents usefully employed include interleukin, especially Interleukin II, TCLF and CBF, separately or in any combination. These other antitumor agents are employed in an effective antitumor amount, equivalent to or the same amount as indicated hereinabove with respect to interferon and/or TNF.

Antiviral surfactants useful in the compositions of this invention include the antiviral anionic, cationic, and nonionic surfactants. Antiviral surface active agents are known, see U.S. Pat. Nos. 4,147,803, 4,020,183, 4,139,630 and 4,507,281. Suitable anionic surfactants include sodium alkylsufonates and sodium alkylbenzenesulfonates. Suitable cationic surfactants include quarternary ammonium detergents, such as cetyl pyridinium chloride, and benzalkonium chlorides.

Nonionic surface active agents are preferred in the compositions of this invention. In contrast to cationic, anionic, and ampholytic surface active agents, the nonionics surface active agents or surfactants contain no ionizable groups and have no surface charge. They depend upon the entire molecule for surface activity. Almost any hydrophobic compound which has in its structure a carboxy, hydroxy, amido or amino group with a free hydrogen attached to the nitrogen, can be reacted with ethylene oxide to form a nonionic surfactant. At least three groups of nonionic surfactants are recognized (a) those having an ether linkage between the hydrophilic and hydrophobic portions of the molecule, (b) those having an ester or etherester linkage, and (c) those having an amide linkage. Nonionic surfactants having at least one ether or amide linkage are preferred for purposes of the present invention. Examples of preferred nonionic surfactants include the following: nonylphenoxypolyethoxy ethanol (available under the trade name Nononxynol-9), p-diisobutylphenoxypolyethoxy ethanol (available under the trade name Triton X-100), polyoxyethylene (10) oleyl ether (available under the trade name Brij-97), and onyx-ol (available under the trade name Onyx-ol 345).

For an effective dosage the antiviral surface active agent for the compositions and purposes of this invention comprises about 0.1% to 20% by weight of the pharmaceutical composition. The preferred range is about 1% to 5% by weight.

The balance of the pharmaceutical compositions comprises a substantially inert, physiologically acceptable carrier. The carrier should not react with the active ingredients and not to reduce their effectiveness. Suitable physiologically acceptable carriers include water, ethanol, polyethylene glycol, mineral oil, petrolatum, propylene glycol, dimethylsulfoxide, and the like. Dimethylsulfoxide is also usefully included in the compositions since diemthylsulfoxide is known to effectively carry drugs past the dermal layer of the skin and as such would be a useful component of the carrier for the composition of this invention. The compositions of this invention, as indicated, are topically applied or administered in formulations suitable for topical application, such as gels, creams, lotions, shampoos, sprays and the like.

The following are examples of suitable formulations of carriers useful in the preparation of compositions in accordance with this invention:

| Pharmaceutical Lotion | |
|---|---|
| propylene glycol | 24.75 ml. |
| triethnolamine | 1.00 ml. |
| water | 7.00 ml. |
| oleic acid | 1.50 gm. |
| polyethylene glycol monostearate | 10.50 gm. |
| silicon fluids | 10.00 ml. |
| carbopol-934 (2% mucilage) | 50.00 ml. |
| Pharmaceutical Cream A | |
| white petrolatum | 41.00 gm. |
| microcrystalline wax | 3.00 gm. |
| fluid lanolin | 10.00 gm. |
| sorbitan monooleate | 4.75 gm. |
| polysorbate-80 | 0.25 gm. |
| purified water | 41.00 gm. |
| Pharmaceutical Cream B | |
| spermaceti | 7.5% |
| white wax | 12.0% |
| mineral oil | 56.0% |
| sodium borate | 0.5% |
| sorbitan monooleate | 5.0% |
| water | 19.0% |

In addition to the components listed above, the antitumor agent, e.g. TNF, Interleukin II, TCLF and/or CBF, preferably in combination with a human interferon in an amount from about $10^2$ IU to $10^8$ IU, would also be included. Additionally, there would be included an antiviral surfactant in the amount 0.05% to about 20% by weight based on the overall composition and, if desirable, a minor amount of dimethylsulfoxide, e.g. an amount in the range about 0.1–10% by weight of the overall composition.

Topical administration of compositions of the present invention may be effected by applying a small amount (e.g., about 1–5 mls) of the compositions directly to and onto the areas adjacent to the site of the lesion with a cotton swab, soft brush, sponge or the like. A quantity sufficient to cover the lesion is usually adequate for treatment. Treatment by topical application of the composition should be regular and, if necessary, frequent, for example, every 2-4 hours, for about 1-7 days, more or less.

The compositions also display antimicrobial activity as well as antitumor and antiviral activity. For example, the compositions are effective in treating certain bacterial infections. As used herein, the term antimicrobial activity refers to activity against microorganisms other than viruses, such as bacteria, yeast and fungi.

In addition to direct topical application of the compositions, the composition may be administered topically by various other methods, for example, by application to the affected skin area in microencapsulated, temperature and/or pressure sensitive form or encapsulated in a film or solid carrier which is soluble in body fluids and the like for subsequent release of the compositions. The compositions may also be delivered in a foam, spray, tampon, suppository, etc.

In another embodiment, the antitumor agent is incorporated in a cosmetic composition containing effective amounts of interferon, the antiviral surfactant, and the antitumor agent, such as TNF and/or Interleukin II, and a physiologically acceptable cosmetic carrier. Additional components, for example, skin softeners, may be included in the cosmetic formulations.

Cosmetic formulations are known in the art and are usually hypoallergenic and pH controlled. The cosmetic formulations of this invention are useful as a prophylactic or for the cosmetic and therapeutic treatment of cancerous skin disorders. Cosmetic formulations according to the present invention generally contain less antitumor agent, human interferon and antiviral surface active agent than the usual therapeutic preparations. The preferred range of the antitumor agent in such compositions is about $10^2$ to about $10^8$ IU The preferred range of human interferon is $10^3$-$10^5$ I.U. and the preferred range of the antiviral surface active agent is 0.1%-5%. A typical carrier for use in a cosmetic formulation according the the present invention has the formulations:

| Cosmetic Cream | |
| --- | --- |
| beeswax | 12.1% |
| spermaceti | 12.6% |
| sweet almond oil | 54.4% |
| borax | 0.5 |
| rose water | 19.4% |

The following examples are illustrative of the practices of this invention:

EXAMPLE 1

A composition in the form of an aqueous gel and containing 2% by weight nonylphenoxypolyethoxy ethanol and a minor amount, about $10^5$ I.U., TNF is applied topically to a cancerous skin lesion, such as a melanoma skin lesion, sufficient to generously cover the skin lesion. After 4 hours another similar application is made and this procedure continued for four days and then discontinued for observation and evaluation before another such series of treatment.

EXAMPLE 2

A composition in accordance with Example 1 is prepared but additionally comprising a minor amount, about $10^5$ I.U. Interleukin II, and is applied similarly to a melanoma skin lesion.

EXAMPLE 3

A composition in accordance with Example 1 is prepared but additionally comprising a minor amount, about $10^5$ I.U., human alpha interferon, and is applied similarly to a melanoma skin lesion.

As would be apparent from the above, the compositions of this invention are also useful when topically applied in the treatment of disseminated or metastasized cancer or tumors. Accordingly, topical application of the composition provides another approach or technique for, in effect, the systemic treatment of cancer or tumors, rather than the conventional intravenous technique.

All the above-identified U.S. patents and the above cited publication are herein incorporated and made part of this disclosure.

As is apparent to those skilled in the art, many changes and modifications and substitutions are possible in the practices of this invention without departing from the spirit or scope thereof.

What is claimed is:

1. A composition comprising an effective antiviral amount of an antiviral surfactant, an effective antitumor amount of an antitumor agent selected from the group consisiting of lymphotoxin, tumor necrosis factor, interleukin, target cell lysis factor and carcino-breaking factor; an effective amount of human interferon and a physiologically acceptable carrier.

2. A composition as in claim 1, wherein the antiviral surfactant is selected from the group consisting of nonylphenoxypolythoxy ethanol, p-dissobutylphenoxypolyethoxy ethanol, polyoxyethylene(10) oleyl ether, and onyx-ol.

3. A composition as in claim 1, wherein the amount of antiviral surfactant is in the range from about 0.1% to about 20% by weight of said composition.

4. A composition of claim 1, wherein the antitumor agent is tumor necrosis factor.

5. A composition of claim 1, wherein said antiviral surfactant is a non-ionic surfactant.

6. A composition of claim 1, wherein said antiviral surfactant is a non-ionic surfactant wherein said antitumor agent is interleukin II.

7. A composition of claim 1, wherein said carrier is a water dispersible carrier or gel.

8. A composition of claim 1, wherein said composition, contains dimethyl sulfoxide.

9. A composition in accordance with claim 1, wherein said antitumor agent is target cell lysis factor.

10. A composition in accordance with claim 1, wherein said antitumor agent is carcino-breaking factor.

11. A composition in accordance with claim 1, wherein said antitumor agent is an interleukin.

12. A composition in accordance with claim 1, wherein said antitumor agent is interleukin II.

13. A composition in accordance with claim 1, wherein said human interferon is alphainterferon.

14. A composition in accordance with claim 1, wherein said human interferon is gamma-interferon.

15. A composition in accordance with claim 1, wherein said human interferon is a mixture of alpha and gamma human interferons.

16. A composition in accordance with claim 1, wherein said antitumor agent comprises a mixture of tumor necrosis factor and interleukin.

17. A composition in accordance with claim 1, wherein said antitumor agent comprises tumor necrosis factor and target cell lysis factor.

18. A composition in accordance with claim 1, wherein said antitumor agent comprises interleukin, target cell lysis factor and carcino-breaking factor.

19. A composition of claim 1 in the form of or provided in a cream, a gel, a lotion, a mouthwash, a spray, a shampoo, a foam. a tampon, or a suppository.

20. A method for treating viral or cancerous skin disorders and skin manifestations thereof which comprises topically administering to the affected skin area an effective amount of a composition in accordance with claim 1.

21. A method of claim 20, wherein said antiviral surfactant is a nonionic surfactant.

22. A method of claim 20, wherein the antiviral surfactant is in the range from about 0.1% to about 20% by weight of said composition.

* * * * *